US009244285B2

(12) United States Patent
Chen et al.

(10) Patent No.: US 9,244,285 B2
(45) Date of Patent: Jan. 26, 2016

(54) INTERFACE USING EYE TRACKING CONTACT LENSES

(71) Applicant: Sony Computer Entertainment Inc., Tokyo (JP)

(72) Inventors: Ruxin Chen, Redwood City, CA (US); Ozlem Kalinli, Burlingame, CA (US)

(73) Assignee: SONY COMPUTER ENTERTAINMENT INC., Tokyo (JP)

( * ) Notice: Subject to any disclaimer, the term of this patent is extended or adjusted under 35 U.S.C. 154(b) by 0 days.

(21) Appl. No.: 14/160,429

(22) Filed: Jan. 21, 2014

(65) Prior Publication Data

US 2014/0198382 A1 Jul. 17, 2014

Related U.S. Application Data

(63) Continuation of application No. 13/101,868, filed on May 5, 2011, now Pat. No. 8,632,182.

(51) Int. Cl.
| | |
|---|---|
| *A61B 3/00* | (2006.01) |
| *G02B 27/22* | (2006.01) |
| *G02C 7/04* | (2006.01) |
| *A61B 3/113* | (2006.01) |

(Continued)

(52) U.S. Cl.
CPC ............ *G02B 27/2235* (2013.01); *A61B 3/113* (2013.01); *G02C 7/04* (2013.01); *G02C 11/10* (2013.01); *H04N 13/0429* (2013.01); *H04N 13/0468* (2013.01); *G02C 2200/02* (2013.01); *H04N 19/162* (2014.11); *H04N 19/167* (2014.11); *H04N 19/597* (2014.11)

(58) Field of Classification Search
CPC .......... A61B 3/125; A61B 3/117; G02C 7/02; G02C 7/04; G02C 7/10; G02B 27/2214; G02B 27/2228; G02B 27/2257; H04N 13/0404
USPC .................. 351/219, 159.01, 159.02, 159.03, 351/159.6, 159.73; 359/462, 466, 464
See application file for complete search history.

(56) References Cited

U.S. PATENT DOCUMENTS

| 4,669,834 A | 6/1987 | Richter | |
|---|---|---|---|
| 5,682,210 A * | 10/1997 | Weirich | ........................ 348/739 |

(Continued)

FOREIGN PATENT DOCUMENTS

EP     1 056 049 A2     11/2000

OTHER PUBLICATIONS

Parviz, Babak, "Augmented Reality in a Contact Lens," http://spectrum.ieee.org/biomedical/bionics, dated Sep. 2009, 5 pages.

(Continued)

*Primary Examiner* — James Greece
(74) *Attorney, Agent, or Firm* — Kilpatrick Townsend & Stockton LLP

(57) ABSTRACT

Methods of eye gaze tracking are provided using magnetized contact lenses tracked by magnetic sensors and/or reflecting contact lenses tracked by video-based sensors. Tracking information of contact lenses from magnetic sensors and video-based sensors may be used to improve eye tracking and/or combined with other sensor data to improve accuracy. Furthermore, reflective contact lenses improve blink detection while eye gaze tracking is otherwise unimpeded by magnetized contact lenses. Additionally, contact lenses may be adapted for viewing 3D information.

13 Claims, 15 Drawing Sheets

(51) Int. Cl.
*G02C 11/00* (2006.01)
*H04N 13/04* (2006.01)
*H04N 19/597* (2014.01)
*H04N 19/162* (2014.01)
*H04N 19/167* (2014.01)

(56) References Cited

U.S. PATENT DOCUMENTS

| | | | |
|---|---|---|---|
| 5,936,705 A | 8/1999 | Ocampo et al. | |
| 7,699,465 B2 | 4/2010 | Dootjes et al. | |
| 7,758,187 B2 * | 7/2010 | Amirparviz | 351/159.28 |
| 2005/0219459 A1 * | 10/2005 | Yoshino | 351/160 R |
| 2007/0121065 A1 | 5/2007 | Cox et al. | |
| 2008/0024722 A1 * | 1/2008 | Pollard | 351/209 |
| 2009/0189830 A1 | 7/2009 | Deering et al. | |
| 2009/0189974 A1 | 7/2009 | Deering | |
| 2009/0213459 A1 * | 8/2009 | Amirparviz | 359/465 |
| 2009/0279736 A1 | 11/2009 | LaConte et al. | |
| 2010/0245767 A1 | 9/2010 | Chao | |

OTHER PUBLICATIONS

Lingley et al., "Multipurpose integrated active contact lenses," http://www.ine-news.org/view.php?article=0056-2008-06-11&category=technologies%3A . . . , printed dated Jun. 30, 2008, 4 pages.

Ziegler, Chris, "Tobii and Lenovo show off prototype eye-controlled laptop, we go eyes-on (video)," www.engadget.com/2011/03/01, dated Mar. 1, 2011, 2 pages.

International Search Report and Written Opinion for corresponding International Application No. PCT/US2012/036618, mailed Dec. 3, 2012, 9 pages.

* cited by examiner

CAMERA VIEW

COMPUTER DISCERNS
CONTACT LENSES

INTERFACE USING EYE TRACKING CONTACT LENSES

CROSS-REFERENCE TO RELATED APPLICATIONS

This is a continuation application of parent U.S. patent application Ser. No. 13/101,868 entitled "Interface Using Eye Tracking Contact Lens," which is hereby incorporated by reference in its entirety for all purposes.

BACKGROUND OF THE INVENTION

1. Field of the Invention

Various embodiments disclosed herein relate to camera and sensor-based tracking of objects, such as a user's head and/or eyes. In particular, contact lenses may be tracked by one or more cameras and/or sensors in order to resolve tracking information, such as position of the objects, the distance between the objects and a camera, and the like. Further embodiments relate to contact lenses used with displays providing three-dimensional (3D) information.

2. Description of the Related Art

Video games have become more immersive as technology progresses. Video game consoles are often produced with state-of-the-art processors, extremely fast memory, and high-end graphics cards. Input controllers have evolved from simple knobs, joysticks, and button-based controllers to accelerometer-enabled controllers that a user can swing in the user's hands or simply wear. Further input technologies involve tracking all or part of a user's body, including tracking the user's head or other facial features, torso, arms, and legs. Users can control such video games by simply moving their bodies or parts thereof. For example, a player of a skateboarding game can duck down so that he or she clears a virtual bridge.

Accordingly, what is desired is to solve problems related to tracking a user or parts of a user's body using contact lens, some of which may be discussed herein. Additionally, what is desired is to reduce drawbacks related to interfacing with computer systems by using contact lenses, some of which may be discussed herein.

Moreover, three-dimensional (3-D, or 3D) televisions and displays help immerse users in events happening on their display screens. For such 3-D televisions, a user sometimes dons 3-D glasses. Earlier 3-D glasses included red and blue lenses for discerning an anaglyph. Shuttered 3-D glasses have lenses that rapidly and alternatingly switch between being opaque and transparent in synchronization with a display that rapidly shows left and right images. Other types of 3-D presentation technology exist. Many are similar in that they present a separate two-dimensional image to a viewer's left eye and a separate two-dimensional image to the viewer's right eye either contemporaneously or very rapidly (e.g., at 120 Hz) in order to trick the viewer's brain into interpreting the stereoscopic images as a 3-D environment.

Video games and augmented reality displays utilizing 3-D display technologies can immerse a player in a game or a user in an augmented reality experience through the use of 3-D effects on the screen. Furthermore, video game consoles and computer systems with body tracking can use 3-D effects to coordinate a user's actual movements in the real world with his or her virtual movement in a displayed virtual world. For example, as a user steps toward the television in his living room, a video game console can render 3-D virtual objects so that they appear like the user moves closer to them. Thus, tracking the location, orientation, and movement of a viewer or other user's head or body parts can be important for some video games and augmented reality experiences.

Accordingly, what is desired is to solve problems related to 3D display technologies using contact lenses for interfacing with computer systems and viewing 3D information, some of which may be discussed herein. Additionally, what is desired is to reduce drawbacks related to 3D display technologies using contact lenses for interfacing with computer systems and viewing 3D information, some of which may be discussed herein.

BRIEF SUMMARY OF THE INVENTION

The following portion of this disclosure presents a simplified summary of one or more innovations, embodiments, and/or examples found within this disclosure for at least the purpose of providing a basic understanding of the subject matter. This summary does not attempt to provide an extensive overview of any particular embodiment or example. Additionally, this summary is not intended to identify key/critical elements of an embodiment or example or to delineate the scope of the subject matter of this disclosure. Accordingly, one purpose of this summary may be to present some innovations, embodiments, and/or examples found within this disclosure in a simplified form as a prelude to a more detailed description presented later.

Methods, systems, computer-readable media, and articles of manufacture are provided for eye gaze tracking using contact lenses and viewing 3D information using contact lenses. In some embodiments, eye gaze may be tracked using magnetic sensors and magnetized contact lenses and/or using video-based sensors and reflective contact lenses. In one embodiment, magnetic sensors may be placed on a video game console or near the head of a user of a video game console to track the location and polarization of magnetized contact lenses. In another embodiment, video-based sensors may be used to track the location of reflective contact lenses transparent to normal light and reflecting one or more portions of the electromagnetic spectrum.

In further embodiments, magnetic sensors and video-based sensors may be used in combination to track a magnetized contact lens with one or more reflective patterns, provide blink detection, and track multiple users. Other video-based sensors may be used to locate the head position of a user and prune noise from other magnetic or other light sources. Additionally, tracking information from contact lenses of both eyes may be used to improve accuracy.

Magnetized and reflective contact lenses may be utilized to browse menus of computer applications, control virtual characters of video games, select-drag-manipulate objects, and perform other trained or learned actions responsive to a user's eye movement or eye gaze. In further aspects, magnetized and reflective contact lenses can be used in any application that can benefit from eye and/or gaze tracking.

In various embodiments, contact lenses are provided for viewing 3D information. Contact lenses in embodiments can be passive (e.g., utilizing color or polarity for 3D viewing) or active, for example, using a liquid crystal layer that is normally transparent but darkens when a voltage is applied.

A further understanding of the nature of and equivalents to the subject matter of this disclosure (as well as any inherent or express advantages and improvements provided) should be realized in addition to the above section by reference to the remaining portions of this disclosure, any accompanying drawings, and the claims.

BRIEF DESCRIPTION OF THE DRAWINGS

In order to reasonably describe and illustrate those innovations, embodiments, and/or examples found within this disclosure, reference may be made to one or more accompanying drawings. The additional details or examples used to describe the one or more accompanying drawings should not be considered as limitations to the scope of any of the claimed inventions, any of the presently described embodiments and/or examples, or the presently understood best mode of any innovations presented within this disclosure.

DETAILED DESCRIPTION OF THE INVENTION

Figure 1:
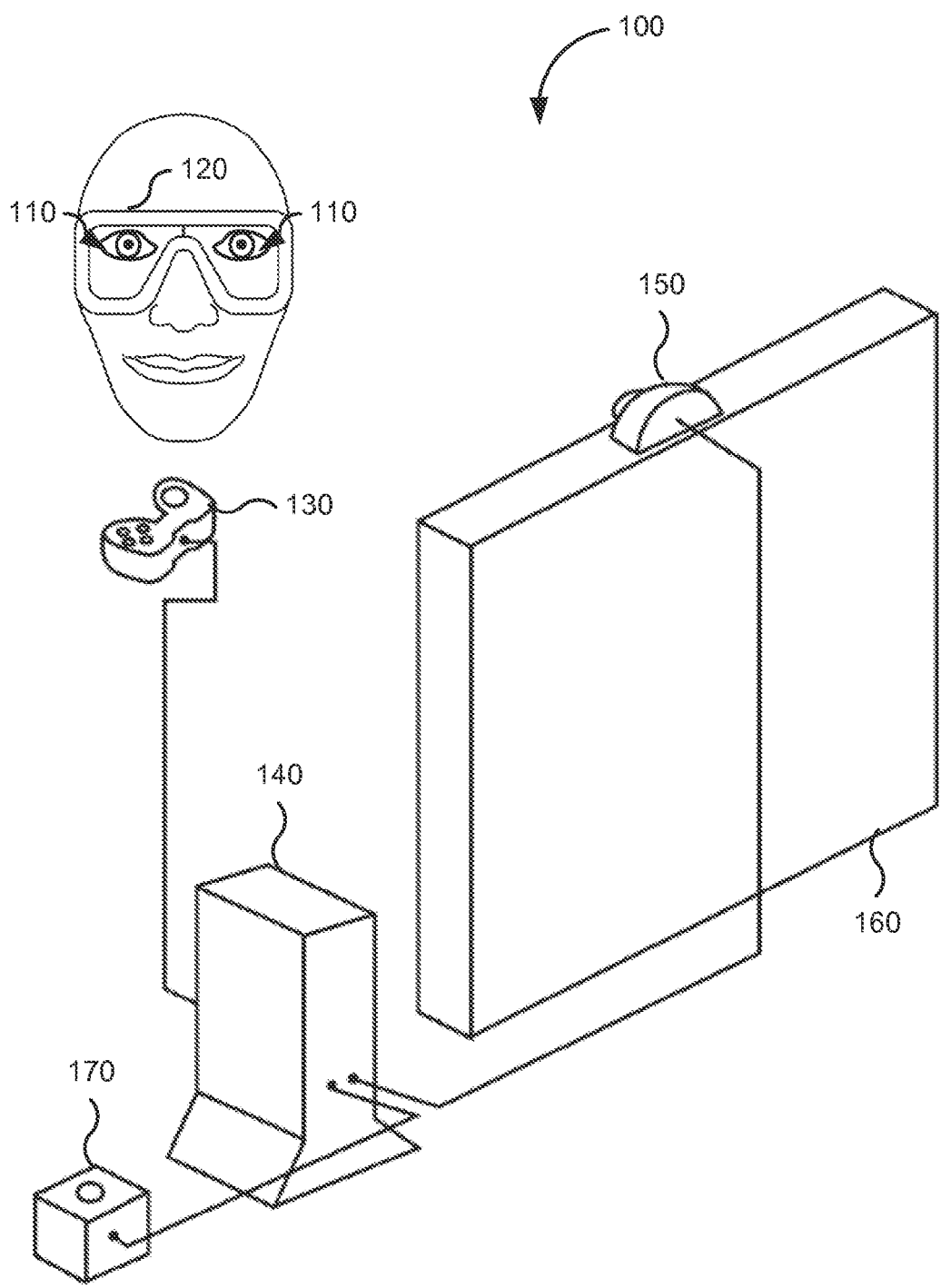
FIG. 1 illustrates a system for eye tracking using contact lenses and/or viewing 3D information using contact lenses in accordance with various embodiments.

Facial tracking is related to body motion capture, but is more challenging due to higher resolution requirements needed to often detect and track subtle expressions possible from small movements of the eyes and lips. These movements can often be less than a few millimeters, requiring even greater resolution and fidelity and different filtering techniques than usually used in full body capture. Eye tracking is the process of measuring either the point of gaze or the motion of an eye relative to another object, such as the head. One or more sensors may measure eye positions and eye movement.

Traditional marker-based systems apply markers to a user's face and track marker movement with one or more sensors, such as high resolution cameras. Unfortunately, these traditional marker-based systems can be relatively cumbersome, such as in medial or industrial scenarios or for players of in-home video game consoles if their entire face needs to be covered in markers to play a video game. Markerless technologies can use the features of the face and eyes such as nostrils, the corners of the lips and eyes, and wrinkles and then track them. While these techniques are much less cumbersome, and allow greater expression, they are mostly ineffective with hardware available to consumer for home computers and video games. Moreover, purchase of needed higher resolution cameras to augment existing home computers and video game systems would be cost prohibitive.

One of the advantages of using contact lenses for eye tracking and viewing 3D information is that they are more practical (i.e., smaller, light weight and easy to carry around) compared to some peripherals used for eye gaze tracking or for 3D information viewing. For example, glasses typically used for 3D information viewing or head-mounts typically used for eye gaze tracking can be complex and cumbersome. In addition, contact lenses can offer highly accurate eye tracking information at low cost. For example, when contact lenses are used for eye gaze tracking, the performance can be better than the one that can be achieved with a camera-based eye tracking solution. Also, compared to camera-based solutions which require expensive high-resolution cameras, contact lenses can offer low cost solutions which make them more suitable for consumer products.

Accordingly, in various embodiments, a combination of marker-based and marker-less eye tracking techniques using contact lenses provide interacting with or controlling objects or menus of a video game, a projected visual user interface, an augmented virtual reality user interface, or the like. In some embodiments, a user may be outfitted with contact lenses that provide for and/or augment the tracking of the users' eyes. In one embodiment, a user may be outfitted with a magnetized contact lens that may be tracked by one or more magnetic sensors positioned on or near a video game console or the user's head. In another embodiment, a user may be outfitted with contact lenses configured for reflecting one or more portions of the electromagnetic spectrum that may be tracked by one or more cameras. In one aspect, the contact lenses may be the only source of tracking information provided to an eye tracking system. In another aspect, the contact lenses may be used to augment and improve existing body, facial, or eye tracking methods and other technologies that can benefit from enhanced eye tracking information.

FIG. 1 illustrates system 100 for eye tracking using contact lenses and/or viewing 3D information using contact lenses in accordance with various embodiments. In this example, a user's eyes are outfitted with contact lenses 110 (e.g., one in each eye). Contact lenses 110 may be suitably configured to provide enhanced eye tracking and/or for viewing 3D information. Optionally, the user's head may be outfitted with glasses 120 in addition to contact lenses 110.

In one example of operation of system 100, a user can use conventional game controller 130 to play a video game provided by video game console 140. Video game console 140 may provide one or more user interfaces, virtual reality interfaces, augmented reality interfaces, or the like when executing one or more applications suitably configured for video game console 140. Alternatively, or in addition to game controller 130, the user can use body movements, facial movements, eye movements, or combinations thereof to provide input to video game console 140. For example, sensor 150, seated in this embodiment on top of display 160, may be embodied as a camera that captures position and movements of the user's body, head, eyes, and/or combinations thereof and feeds them to video game console 140. As the user swings the user's head and/or moves the user's eyes to interact with the video game, for example, sensor 150 tracks the user's head and eyes using facial and eye tracking techniques. Eye tracking data can be further combined with other body movements, gestures, and tracking information for controlling a game or interacting with various user interfaces, etc. (e.g., if a subject stares at an object and moves his arm down, this can mean dropping an object selected via eye gaze tracking).

Accordingly, position and orientation of the user's body, head, eyes, and other body and facial features may be determined during time period $t_1$ through $t_3$ by one or more sensors. Some examples of sensors can include video-based sensors (e.g., cameras) and magnetic sensors. In one example, sensors may determine position and orientation of the user's head at one position p-head$_1$ and orientation o-head$_1$ at time $t_1$, another position p-head$_2$ and orientation o-head$_2$ at time $t_2$, and a further position p-head$_3$ and orientation o-head$_3$ at time $t_3$. The user's left eye may be at one position p-leye$_1$ and orientation o-leye$_1$ at time $t_1$, another position p-leye$_2$ and orientation o-leye$_2$ at time $t_2$, and a further position p-leye$_3$ and orientation o-leye$_3$ at time $t_3$. The user's right eye may be at one position p-reye$_1$ and orientation o-reye$_1$ at time $t_1$, another position p-reye$_2$ and orientation o-reye$_2$ at time $t_2$, and a further position p-reye$_3$ and orientation o-reye$_3$ at time $t_3$. The user's head and eyes may move in any direction and at any rotation during time period $t_1$ through $t_3$. Other positions, orientations, and ranges of motion may be determined by sensors associated with system 100.

Facial and eye tracking algorithms can be integral with camera 150 or be part of software or hardware in video game console 140. In other embodiments, tracking logic can be in yet a separate device. As discussed further below, vision-based approaches may be used to track eye and pupil movement, eyelids, and blinks. Alternatively, or in addition to such vision-based approaches, another sensor 170, such as embodied as a magnetic sensor, may be used to track eye and pupil movement, eyelids, etc.

In another example of operation of system 100, a user can view 3D information on display 160 using contact lenses 110. For example, display 160 includes hardware and/or software elements capable of conveying 3D information. In one aspect, display 160 provides a stereoscopic perception of 3-D depth to the viewer for video games hosted by video game system 140.

In this example, system 100 includes hardware and/or software elements consistent with a video game system for playing one or more video games or a home theater system for viewing media, such as 3D information. System 100 may include more or less elements and may be embodied as any number of computer systems, independent or cooperative devices, televisions and/or monitors, portable or embedded devices, and the like.

Eye Tracking Using Contact Lenses

Figures 2, 3:
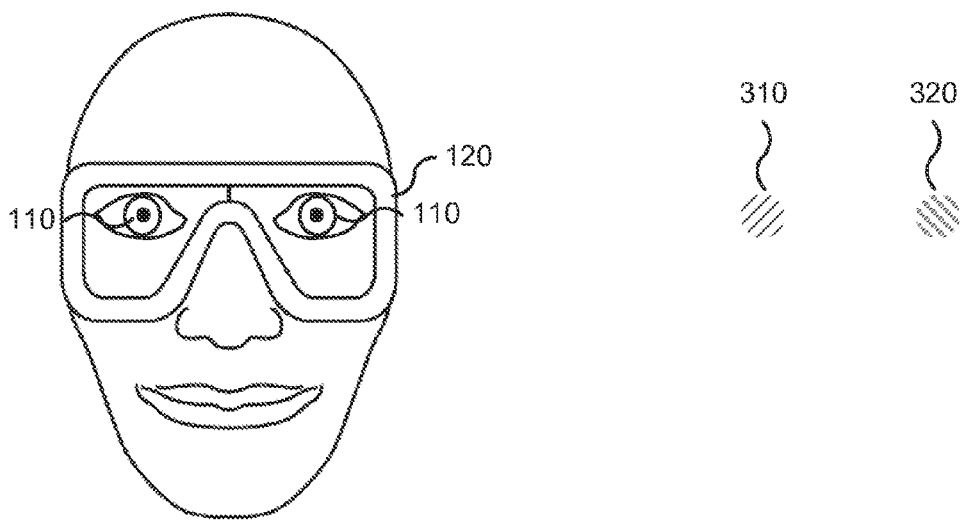
FIG. 2 illustrates a view of a user's face in accordance with an embodiment.
FIG. 3 illustrates recognition features of FIG. 2 as discerned by the system of FIG. 1 in accordance with an embodiment.

FIG. 2 illustrates a view of a user's face in accordance with an embodiment as observed by one or more sensors, such as a camera. The user's head and/or face may be illuminated by one or more illumination sources, such as the sun, normal room lighting, or other lighting sources aimed directly or indirectly at the user head and/or face to be observed by the camera. The user's face has facial features such as eyes (observed in the figure with contact lenses 110 and through glasses 120), a nose, and a mouth. Other facial or head features can be recognized by the camera as known in the art. For example, a user's ear lobes may be tracked along with other features.

FIG. 3 illustrates recognition features of FIG. 2 as discerned by a computer in accordance with an embodiment. Eye area 310 is correlated with an area covered by or corresponding to one of contact lenses 110 placed over the user's right eye. Eye area 320 is correlated with an area covered by or corresponding to one of contact lenses 110 placed over the user's left eye. Other features, such as a nose area may be correlated with the user's nose and a mouth area may be correlated with the user's mouth. Other methods and features for facial tracking are contemplated, and one of skill in the art would recognize the applicability of facial tracking algorithms in light of this disclosure.

Figure 4:
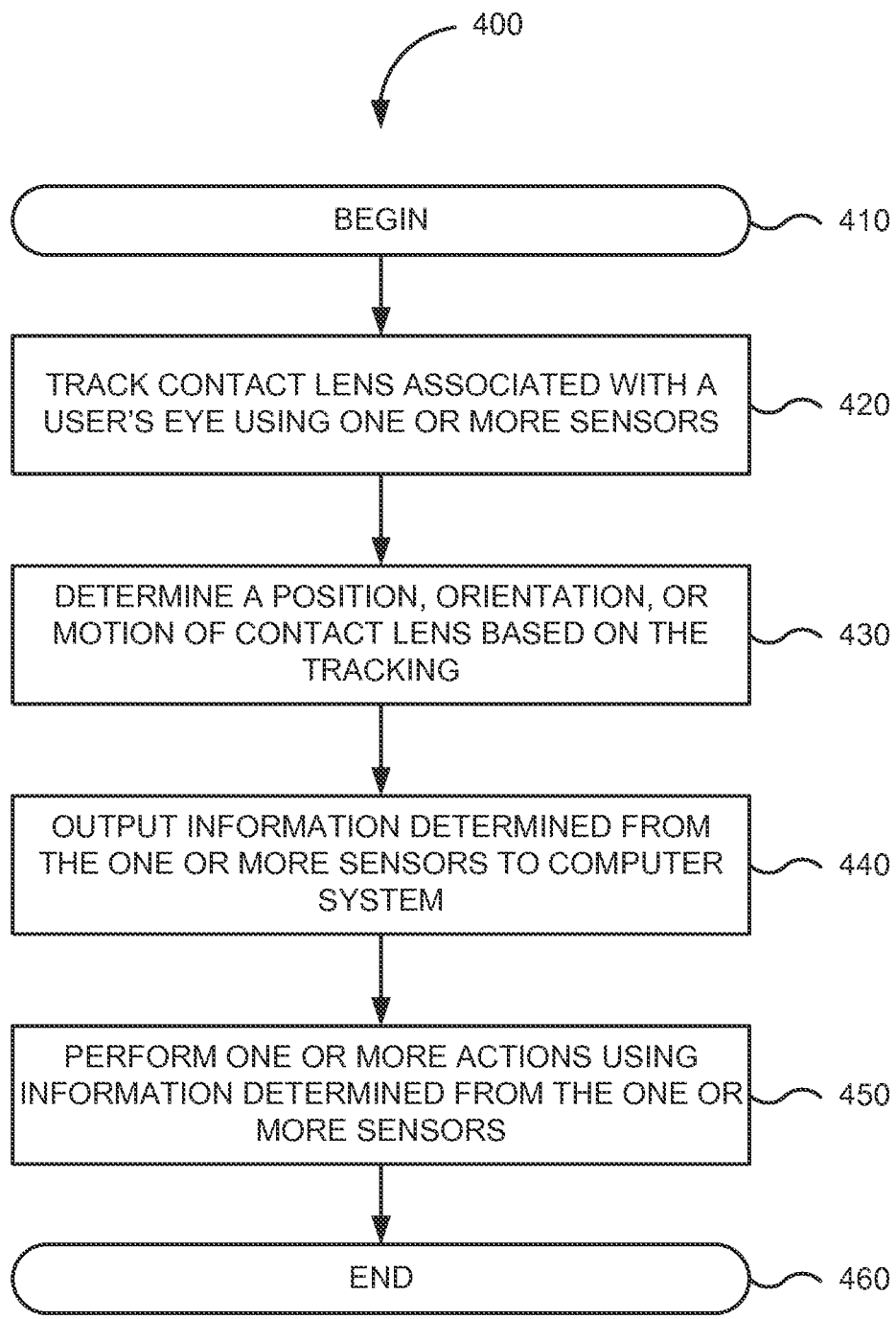
FIG. 4 is a simplified flowchart of a method for tracking recognition features derived in whole or in part from contact lenses in accordance with an embodiment.

FIG. 4 is a simplified flowchart of method 400 for tracking recognition features derived in whole or in part from contact lenses in accordance with an embodiment. Implementations of or processing in method 400 depicted in FIG. 4 may be performed by software (e.g., instructions or code modules) when executed by a central processing unit (CPU or processor) of a logic machine, such as a computer system or information processing device, by hardware components of an electronic device or application-specific integrated circuits, or by combinations of software and hardware elements. Method 400 depicted in FIG. 4 begins in step 410.

In step 420, a contact lens associated with a user's eye is tracked using one or more sensors. In some embodiments, a user may be outfitted with magnetized or magnetic contact lenses that may be tracked by one or more magnetic sensors positioned on or near a video game console or the user's head. For example, one or more magnetic sensors may measure the location and polarization of a magnetized contact lens. In another example, one or more magnetic sensors may measure how a magnetic contact lens interferes or interacts with an existing magnetic field. In a further example, one or more magnetic sensors may measure differences between a contact lens' relative positions in multiple magnetic fields.

In further embodiments, a user may be outfitted with contact lenses configured for reflecting one or more portions of the electromagnetic spectrum that may be tracked by one or more video-based sensors. Traditionally, a camera or another computer system receiving a camera feed may use image processing to locate the center of the pupil and contrast such with infrared and near-infrared non-collimated light to create a corneal reflection (CR). In various embodiments, contact lenses may be configured with one or more reflecting patterns that reduce or otherwise eliminate the need for processing to locate the center of the pupil. For example, a camera may focus on one or both eyes and record their movement. A video-based eye tracker may use a sampling rate of at least 30 Hz. Although 50/60 Hz is most common, video-based eye trackers may run at 240, 350 or even 1000/1250 Hz in order to capture specific details, such as very rapid eye movement.

In further embodiments, a user may be outfitted with magnetic contact lenses configured for reflecting one or more portions of the electromagnetic spectrum that may be tracked by one or more magnetic sensors and one or more video-based sensors.

In step 430, a position, orientation, or motion of the contact lens is determined based on the tracking Eye movement is typically divided into fixations and saccades, when the eye gaze pauses in a certain position, and when it moves to another position, respectively. The resulting series of fixations and saccades is called a scanpath. Therefore, fixations along a scanpath may be used to interact with a video game system, control a video game, or participate in an augmented reality experience. Additionally, saccades along a scanpath may be used to interact with a video game system, control a video game, or participate in an augmented reality experience.

In some aspects, the one or more sensors may measure the rotation of the eye with respect to each of the one or more sensors. If a sensor is head mounted, then the sensor may measure eye-in-head angles. For head-mounted trackers, head position and direction may be added to eye-in-head direction to determine gaze direction. If a sensor is mounted remotely from the user's head, then the sensor may measure gaze direction. For remotely mounted systems, head direction may be subtracted from gaze direction to determine eye-in-head position.

In step 440, information determined from the one or more sensors is output to a computer system. In step 450, one or more actions are performed using the information from the one or more sensors. Some examples of actions that may be performed may include starting an application, interacting with an application, closing an application, controlling a video game character, navigating a virtual world, selecting menu items, forming words, drawing, scrolling, and the like. FIG. 4 ends in step 460.

Figure 5:
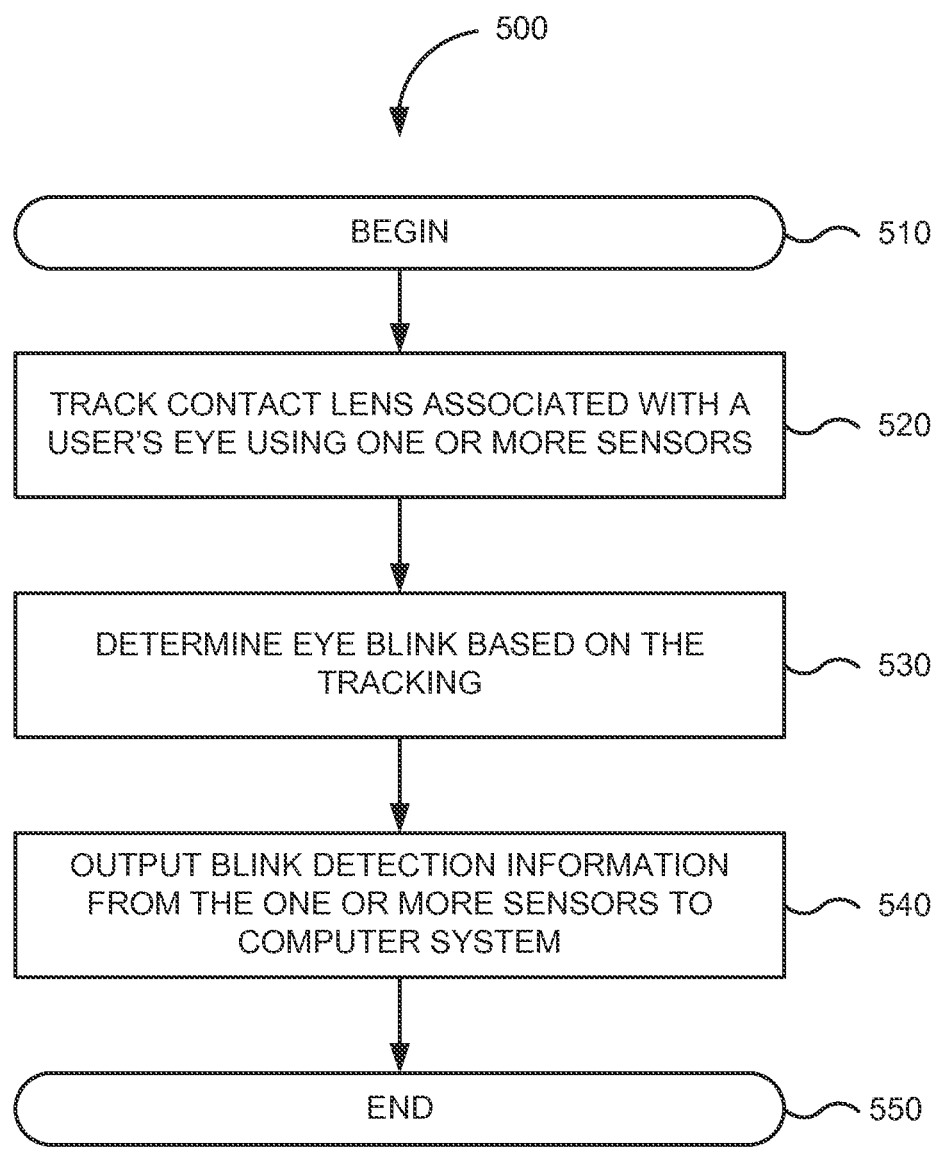
FIG. 5 is a simplified flowchart of a method for blink detection using contact lenses in accordance with an embodiment.

FIG. 5 is a simplified flowchart of method 500 for blink detection using contact lenses in accordance with an embodiment. Implementations of or processing in method 500 depicted in FIG. 5 may be performed by software (e.g., instructions or code modules) when executed by a central processing unit (CPU or processor) of a logic machine, such as a computer system or information processing device, by hardware components of an electronic device or application-specific integrated circuits, or by combinations of software and hardware elements. Method 500 depicted in FIG. 5 begins in step 510.

In step 520, a contact lens associated with a user's eye is tracked using one or more sensors. In some embodiments, a user may be outfitted with magnetized contact lenses that may be tracked by one or more magnetic sensors positioned on or near a video game console or the user's head. In further embodiments, a user may be outfitted with contact lenses configured for reflecting one or more portions of the electromagnetic spectrum that may be tracked by one or more video-based eye trackers. In still further embodiments, a user may be outfitted with magnetized contact lenses configured for reflecting one or more portions of the electromagnetic spectrum that may be tracked by a combination of one or more magnetic sensors and one or more video-based eye trackers.

In step 530, one or more eye blinks are determined based on the tracking. An eye blink may be a full or partial closure of the eye. In one aspect, an eye blink is determined based on a gap in tracking information of a user's eye that satisfies predetermined criteria. A gap in the tracking information may be introduced by a momentary closure of the user's eye. In some embodiments, a user is outfitted with a contact lens tracked by one or more magnetic sensors and one or more video-based sensors. A gap may be introduced when closure of the user's eye interrupts detection of one or more reflective patterns associated with the contact lens. Thus, whenever a user blinks the strength of reflected light from a reflective contact lens is reduced, often drastically. In some embodiments, the one or more video-based sensors can detect the closure of the user's eye while magnetic sensors keep track where the eye is even when the eye is closed. A combination of camera output and magnetic sensors output help to improve the tracking and determination of eye-blinking One or more rules or criteria may be defined to detect a blink when a magnetic field is detected or interfered with or when the strength of reflected light from a reflective contact lens is reduced below a predetermined limit or threshold and/or for a predetermined amount of time.

In step 540, blink detection information is output from the one or more sensors to a computer system. In various embodiments, blink detection may occur at the computer system based on an analysis of raw sensor data obtained from the one or more sensors. As discussed above, one or more actions may be performed when one or more blinks are detected. Some examples of such actions may include controlling a video game (i.e., selecting or dropping an object), interacting with an application, or the like. FIG. 5 ends in step 550.

Figure 6:
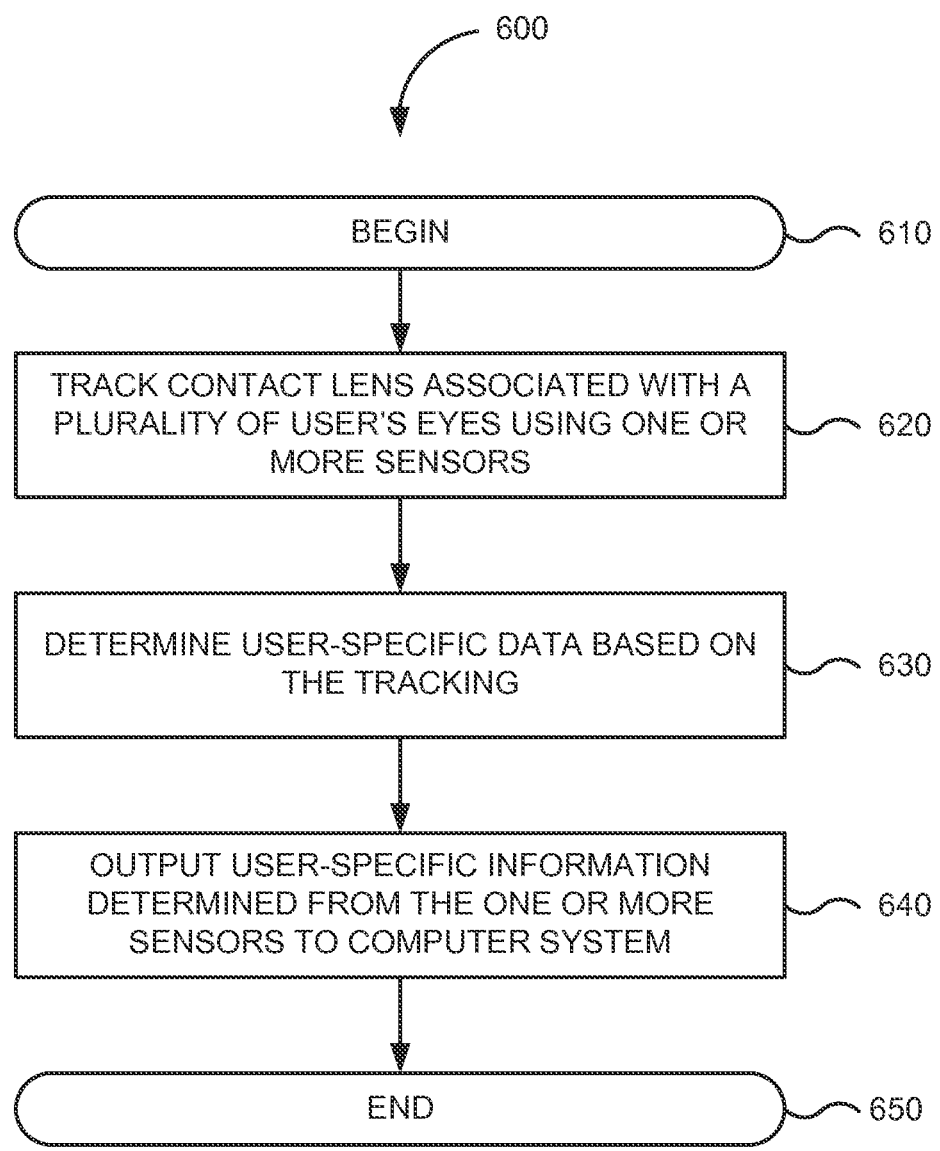
FIG. 6 is a simplified flowchart of a method for tracking recognition features of different users using contact lenses in accordance with an embodiment.

FIG. 6 is a simplified flowchart of method 600 for tracking recognition features of different users using contact lenses in accordance with an embodiment. Implementations of or processing in method 600 depicted in FIG. 6 may be performed by software (e.g., instructions or code modules) when executed by a central processing unit (CPU or processor) of a logic machine, such as a computer system or information processing device, by hardware components of an electronic device or application-specific integrated circuits, or by combinations of software and hardware elements. Method 600 depicted in FIG. 6 begins in step 610.

In step 620, contact lenses associated with a plurality of users' eyes are tracked using one or more sensors. In some embodiments, each user may be outfitted with magnetized contact lenses that may be tracked by one or more magnetic sensors positioned on or near a video game console or each user's head. In some embodiments, each user may be outfitted with contact lenses configured for reflecting one or more portions of the electromagnetic spectrum that may be tracked by one or more video-based eye trackers. In some embodiments, each user may be outfitted with magnetic contact lenses configured for reflecting one or more portions of the electromagnetic spectrum that may be tracked by one or more magnetic sensors and one or more video-based sensors. Contact lenses of different users may reflect a different portion of the electromagnetic spectrum. Contact lenses of different users may further reflect different patterns.

In step 630, user-specific data is determined based on the tracking. For example, a position, orientation, or motion of the contact lens of each individual user may be determined based on the tracking. In another example, fixations and saccades of each individual user may be logged.

In step 650, user-specific information is output from the one or more sensors to a computer system. FIG. 6 ends in step 650.

Magnetic Sensors and Contact Lenses

Generally, one or more magnetic sensors may be configured to detect position and/or movement of a contact lens attached in some way to a user. Preferably, a magnetized contact lens is constructed so as to provide a magnetic field having a predetermined polarization and not to obstruct the view of a user. Additionally, a magnetic contact lens may be constructed so as to interfere with an external magnetic field in a manner detectable to one or more magnetic sensors and not to obstruct the view of a user.

Figure 7:
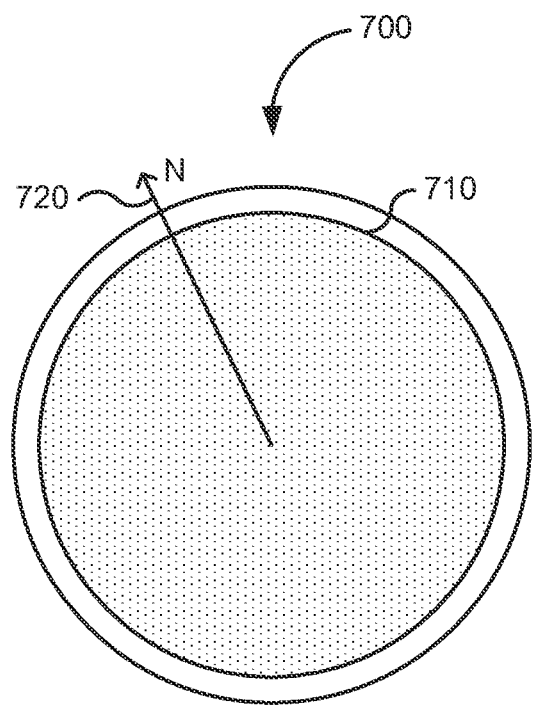
FIG. 7 is an illustration depicting a magnetized contact lens in accordance with an embodiment.

FIG. 7 is an illustration depicting magnetized contact lens 700 in accordance with an embodiment. In this example, contact lens 700 includes several magnetic elements that are widely distributed throughout area 710 of contact lens 700. The magnetic elements are configured to produce a magnetic field having magnetic pole 720. Magnetic pole 720 may be perpendicular to contact lens 700. Magnetic pole 720 may be configured in a variety of polarizations through orientation of the magnetic elements.

In some aspects, the magnetic elements of contact lens 700 are configured of an appropriate size and appropriately distributed such that the magnetic elements do not significantly block or otherwise disturb a wearer's vision. The magnetic elements of contact lens 700 may further be configured of a transparent or semi-opaque magnetized material.

In various embodiments, contact lens 700 has the magnetized particles embedded therein. In further embodiments, contact lens 700 may have the magnetized particles affixed one or more outer surfaces of contact lens 700. In some aspects, contact lens 700 may be manufactured by having the magnetized particles embedded in contact lens 700 during manufacture. In other aspects, contact lens 700 may be manufactured by having non-magnetized particles embedded in contact lens 700 during manufacture, which are later magnetized by an external magnetic field. In some aspect, magnetized contact lenses can optionally be designed such that they can be worn on top of a regular contact lens which a user might be using for improving his/her vision.

Figure 8:
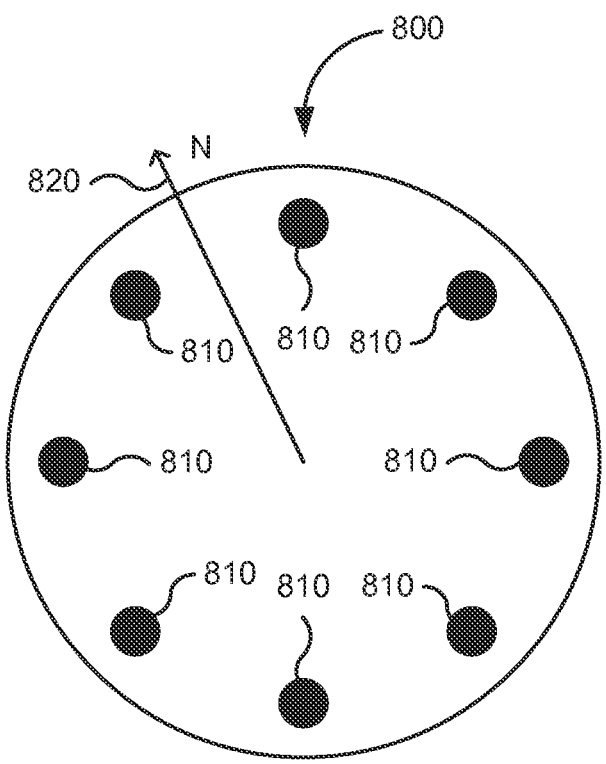
FIG. 8 is an illustration depicting another magnetized contact lens in accordance with an embodiment.

Different distributions of magnetic elements or material in contact lens 700 typically produce different magnetic fields. Thus, these different distributions may result in different systematic relationships between sensor measurements and eye positions. However, methods for translating sensor outputs to eye position described herein do not depend on the exact arrangement of magnetic material associated with the eye, and thus a wide range of arrangements may be used. Specifically, FIG. 8 is an illustration depicting contact lens 800 in accordance with an embodiment. In this example, contact lens 800 includes a radially symmetric arrangement of magnetic elements distributed evenly around the circumference of contact lens 800.

In general, embodiments that produce larger magnetic fields (more, stronger magnetic material) are preferred, as they will produce the largest variation in sensor output as the eye moves. In some aspects, magnetic elements may be packed more densely on one or more sides of a magnetized contact lens. In various embodiments, clustered magnetic elements may be located only on the side of a magnetized contact lens that is closest to a magnetic sensor.

The magnetic element of a magnetized contact lens in an embodiment may comprise a wide choice of materials, for example, any ferromagnetic material, including neodymium-iron-boron, FeCoB, FeCoNiB, an alloy material comprising iron, nickel and/or cobalt, at least one element selected from the group consisting of Fe (iron), Co (cobalt), Ni (nickel), Ti (titanium), Zn (zinc), Cr (chrome), V (vanadium), Mn (manganese), Sc (scandium), and Cu (copper). Neodymium-iron-boron alloys are preferred as they generally produce the strongest magnetic fields. In another embodiment, a magnetic or magnetized contact lens may comprise a material that exhibits super paramagnetism. In another embodiment, a magnetic or magnetized contact lens may comprise iron oxide nanoparticles. In another embodiment, a magnetic or magnetized contact lens may comprise any other magnetic material known in the art.

In another embodiment, a magnetic contact lens associated with a wearer's eye may not itself generate a magnetic field, but rather, may distort an external magnetic field in the vicinity of the magnetic contact lens. Such a magnetic contact lens may comprise a wide range of materials of magnetic permeabilities.

In various embodiments, one or more magnetic sensors configured to detect position and/or movement of a contact lens may be attached in some way to a user. Preferably, one or more magnetic sensors are attached so as not to obstruct the view of the user or interfere, for example, with a user's interaction with a video game console. Of course, any number of magnetic sensors may be attached to any part of the body or article associated with any part of the body. For example, one or more magnetic sensors may be attached to a helmet, eyeglasses, goggles, backpack, belt, etc.

Figure 9:
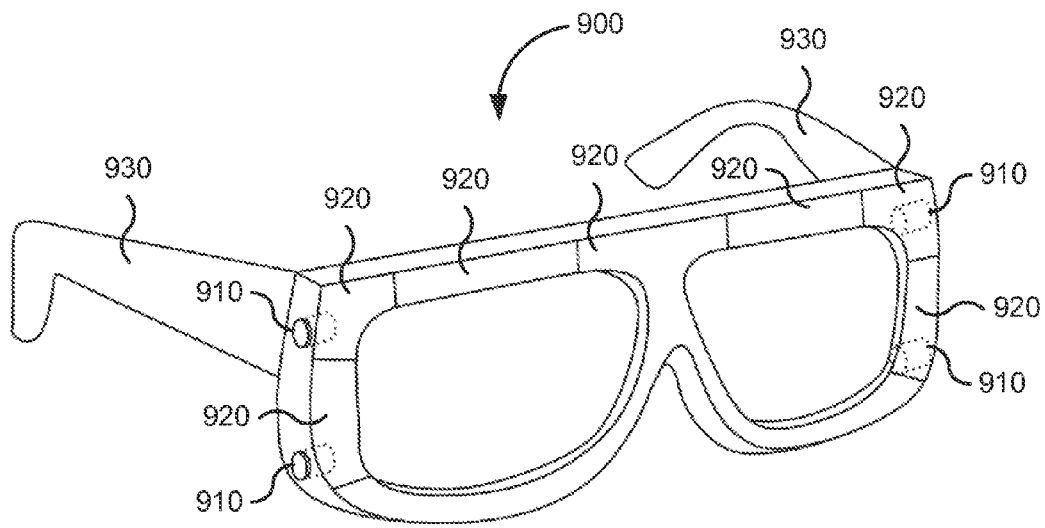
FIG. 9 is an illustration depicting glasses that may be worn by a user having one or more sensors configured to track magnetized contact lenses in accordance with an embodiment.

FIG. 9 is an illustration depicting glasses 900 that may be worn by a user having one or more sensors configured to track magnetized contact lenses in accordance with an embodiment. In this example, magnetic sensors 910 and 920 are embedded into or on the frame of glasses 900. Arrangement of magnetic sensors 910 and 920 in or on glasses 900 may be provided to maximize detection of changes in a magnetic field provided by a magnetized contact lens or interference caused by a magnetic contact lens in an external magnetic field.

Figure 10:
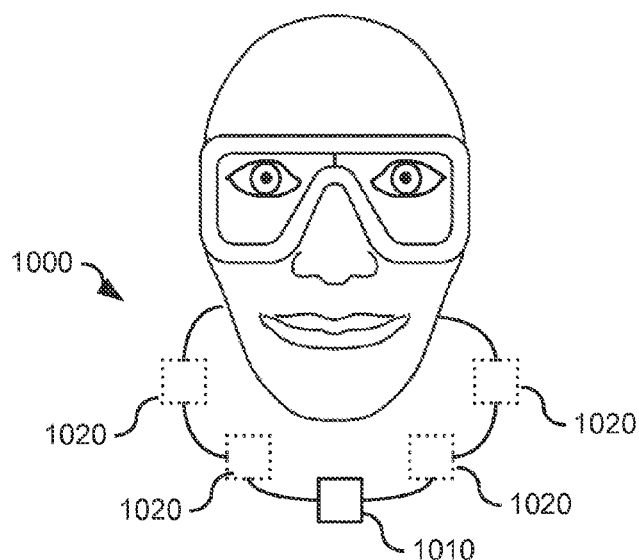
FIG. 10 is an illustration depicting one or more sensors that may be worn around the neck of a user for tracking magnetized contact lenses having a magnetic polarity in accordance with an embodiment.

FIG. 10 is an illustration depicting magnetic sensors 1010 and optional magnetic sensors 1020 that may be worn around the neck of a user for tracking magnetized contact lenses in accordance with an embodiment.

Exemplary magnetic sensors may be any of the following Honeywell sensors: HMC1001, HMC1002, HMC1021S, HMC1021Z, HMC1021D, HMC1022, HMC1023, HMC1041Z, HMC1051Z, HMC1051ZL, HMC1052, HMC1052L, HMC1053, HMC1055, HMC1501, HMC1512, HMC6352, and HMC2003; and any of the following NVE Corporation magnetic sensors: the AA-Series, AAH-Series, and AAL-Series GMR Magnetometer sensors and the AB-Series and ABH-Series GMR Gradiometer sensors, or any other magnetic sensors known in the art. Other examples include magnetoresistive sensors based on the spin-dependent tunneling junctions and sensors that measure the Hall Effect produced by a magnetic field (e.g. Honeywell SS4, SS5, SS400 and SS500). The use of magnetic sensors is well known in the art, and can be obtained, for example, from the literature accompanying any of the above sensors.

In another embodiment, a set of magnetic sensors may include a differential sensor. A differential sensor may further include a plurality of single-axis sensors, the single-axis sensors having identical or similar orientations. A differential sensor is typically one that computes the difference in magnetic fields detected by two like-oriented sensors, here referred to as a "differential pair" of sensors. However, the differential sensor may also be any other type of differential sensor known in the art. To the extent that sensors in a "differential pair" are oriented in similar directions, the impact of interfering magnetic sources on the measured signals may be more similar (particularly if the interfering source is far away and the two sensors in the pair are close to each other). Thus, taking the difference between the outputs of sensors in a differential pair may be used to cancel-out some of the effect of interfering magnetic sources.

In one embodiment, the distance between the sensors in a differential pair and a magnetized contact lens may be small relative to the distance between the pair and an interfering magnetic source (e.g. the Earth's magnetic field, a cathode-ray tube (CRT) monitor, or a building's power distribution). This enables an accurate calculation of the field generated by the magnetized contact lens, because differences between the flux sensed by the sensors of the differential pair will typically be greater from the nearby (eye-associated) article, as compared with a distant interfering source.

Video-Based Sensors and Contact Lenses

Generally, one or more video-based sensors may be configured to detect position and/or movement of a reflective contact lens attached in some way to a user. Preferably, a reflective contact lens is constructed so as not to obstruct the view of the user or interfere, for example, with a user's interaction with a video game console.

Figure 11:
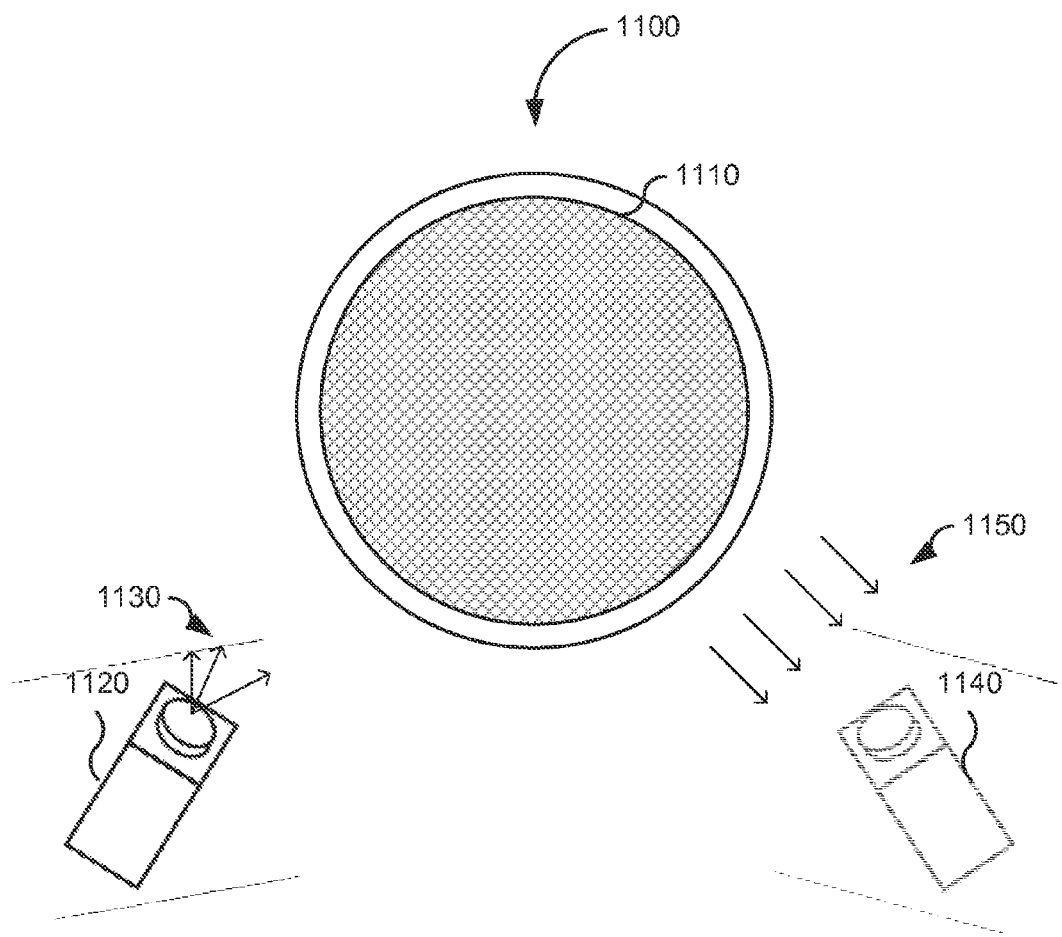
FIG. 11 is an illustration depicting a contact lens configured for reflecting a portion of the electromagnetic spectrum in accordance with an embodiment.

FIG. 11 is an illustration depicting contact lens 1100 configured for reflecting a portion of the electromagnetic spectrum in accordance with an embodiment. In this example, contact lens 1100 includes reflective element 1110. Reflective element 1110 is configured to be transparent to normal light and to reflect infrared (IR) or near infrared (NIR) light. For example, a source of IR or NIR light (e.g., source 1120) may generate a plurality of incoherent and/or coherence rays 1130 to illuminate reflective elements 1110. A detector of IR or NIR light (e.g., sensor 1140) may gather a plurality of incoherent and/or coherence rays 1150 reflected from reflective elements 1110.

Figure 12:
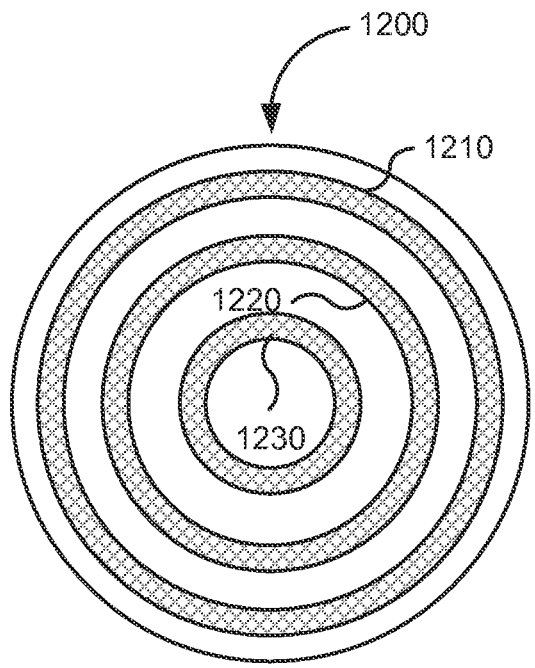
FIGS. 12, 13, and 14 are illustrations depicting different examples of patterns that may be provided on contact lenses for reflecting a portion of the electromagnetic spectrum in accordance with various embodiments.
Figure 13:
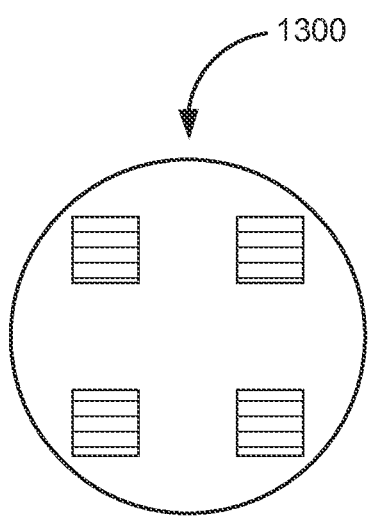
Figure 14:
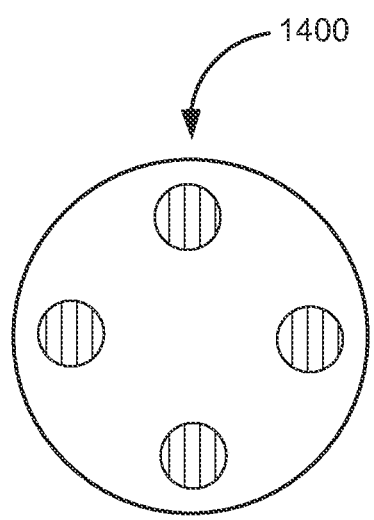

FIGS. 12, 13, and 14 are illustrations depicting different examples of patterns that may be provided on contact lenses for reflecting a portion of the electromagnetic spectrum in accordance with various embodiments. In FIG. 12, contact lens 1200 includes circular bands 1210, 1220, and 1230. Each of circular bands 1210, 1220, and 1230 are configured to reflect IR or NIR light. Width of circular bands 1210, 1220, and 1230 can be consistent or variable between bands.

In various aspects, the number of reflective areas in one contact lens to the next can be varied to define a specific pattern. In further aspects, the shape of reflective areas from one contact lens to the next can be varied to define a specific pattern. In still further aspects, reflective areas may be perceived as solid areas or as containing fill patterns. The number, shape, fill pattern, and the like of reflective areas can be varied based on detection routines or to distinguish between individual eyes or individual users. In FIG. 13, for example, contact lens 1300 includes at least four square shaped reflective areas. Placement of each reflective square shape may be in a square pattern with each reflective square shape placed at a corner of the square pattern. In FIG. 14, for example, contact lens 1400 includes at least four circular reflective areas. Placement of each reflective circle area may be in a circular pattern with each reflective circle shape placed around the circumference of contact lens 1400. Other patterns for reflective areas may be provided, such that eye tracking accuracy is improved.

Improving Accuracy of Eye Tracking

Figure 15:
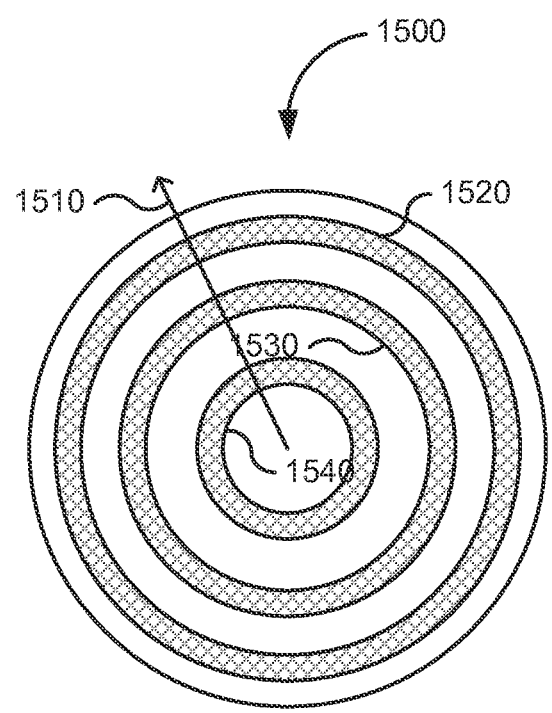
FIG. 15 is an illustration depicting a magnetized contact lens configured for reflecting a portion of the electromagnetic spectrum in accordance with an embodiment.

In various embodiments, accuracy of eye tracking using contact lenses can be improved using magnetic contact lenses having one or more reflective patterns. FIG. 15 is an illustration depicting magnetized contact lens 1500 configured for reflecting a portion of the electromagnetic spectrum in accordance with an embodiment. In this example, contact lens 1500 includes several magnetic elements that are widely distributed throughout contact lens 1500. The magnetic elements are configured to produce a magnetic field having magnetic pole 1510. Magnetic pole 1510 may be perpendicular to contact lens 1500. In some aspects, the magnetic elements of contact lens 1500 are configured of an appropriate size and appropriately distributed such that the magnetic elements do not significantly block or otherwise disturb a wearer's vision. The magnetic elements of contact lens 1500 may further be configured of a transparent or semi-opaque magnetized material. Contact lens 1500 further includes circular bands 1520, 1530, and 1540. Each of circular bands 1520, 1530, and 1540 are configured to reflect IR or NIR light. Width of circular bands 1520, 1530, and 1540 can be consistent or variable between bands.

Figure 16:
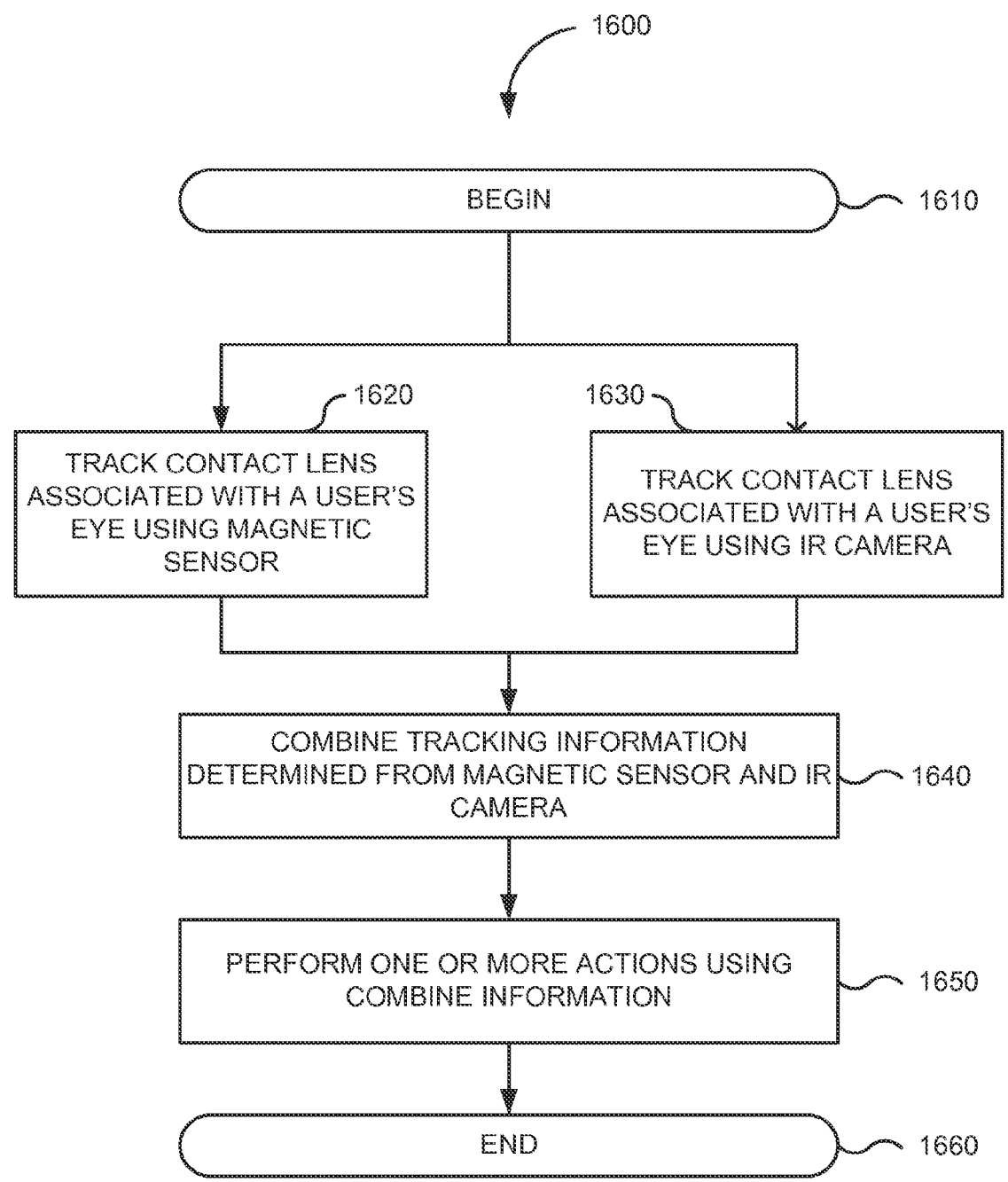
FIG. 16 is a flowchart of a method for eye tracking using magnetized and reflective contact lenses in accordance with an embodiment.

FIG. 16 is a flowchart of method 1600 for eye tracking using magnetized and reflective contact lenses in accordance with an embodiment. Implementations of or processing in method 1600 depicted in FIG. 16 may be performed by software (e.g., instructions or code modules) when executed by a central processing unit (CPU or processor) of a logic machine, such as a computer system or information processing device, by hardware components of an electronic device or application-specific integrated circuits, or by combinations of software and hardware elements. Method 600 may set forth steps as occurring one after the other, however some of the steps may be performed or otherwise implemented in any order, including simultaneously and in parallel. Method 1600 depicted in FIG. 16 begins in step 1610.

In step 1620, a contact lens associated with a user's eye is tracked using one or more magnetic sensors. As in FIG. 15, a user may be outfitted with magnetized contact lenses that may be tracked by one or more magnetic sensors positioned on or near a video game console or the user's head. In step 1630, a contact lens associated with a user's eye is tracked using one or more video-based sensors, such as an IR or NIR camera. As in FIG. 15, the user may be outfitted with contact lenses configured for reflecting one or more portions of the electromagnetic spectrum that may be tracked by one or more video-based eye trackers. Steps 1620 and 1630 can be executed in parallel.

In step 1640, tracking information from the one or more magnetic sensors is combined with tracking information from the one or more video-based sensors. For example, an initial position, orientation, or motion of a contact lens may be determined and then updated to subsequent position, orientation, or motion based on the combined tracking. In other aspects, the one or more video-based sensors may measure position of a user's head or eyes while one or more magnetic sensors track location of the magnetized contact lenses. In further embodiments, both sensors may be used to improve the accuracy of the other. In still further embodiments, other sensors may be used to filter noise (e.g., light and magnetic noise) and provide course location information to be improved by the magnetized or video-based sensors. In other embodiments, information from one eye can be used to track the other eye.

In step 1650, one or more actions are performed using the information from the one or more sensors. One example of actions that may be performed may include browsing menus in response to a user rolling their eyes toward the left, right, up, or down. Another example may include controlling objects in a video game using eye blinking, such as selecting/deselecting objects, picking up or dropping objects, or double clicking Yet further examples may include dragging objects using eye movements, staring to activate firing, or the like. In some aspects, a learning system may be used to map a user's eye tracking information to one or more actions that may be performed. FIG. 16 ends in step 1660.

3D Information and Contact Lenses

For certain uses, contact lenses have the advantage of being much lighter and smaller than glasses. These features can be especially useful when watching/playing 3D content for long periods of time. Thus, in various embodiments, contact lenses can provide for viewing 3D information instead of or together with 3D glasses. 3D contact lenses can be useful in other fields, such as in the medical field for surgeons to practice various procedures or interact remotely as well as in industry for view 3D information or controlling robots.

Figure 17A:
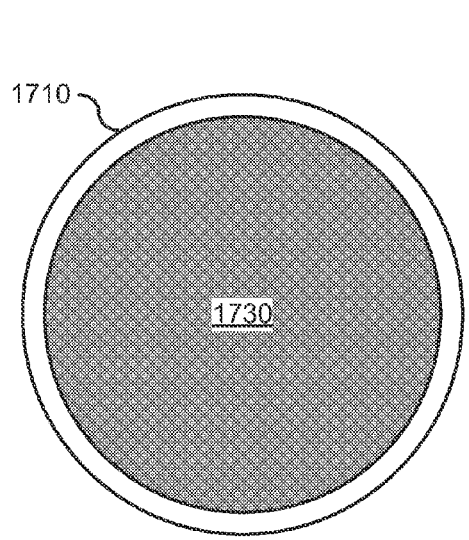
FIGS. 17A and 17B are illustrations depicting contact lenses having colored areas configured for filtering left and right images of a 3-D display in accordance with one embodiment.
Figure 17B:
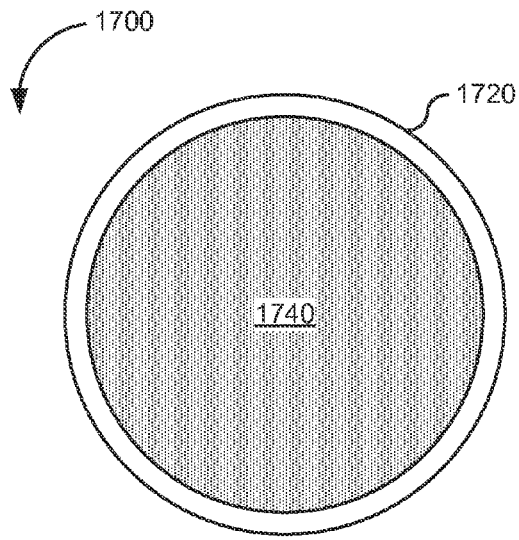

In some embodiments, contact lenses may be used to view anaglyph images. In general, anaglyph images are used to provide a stereoscopic 3D effect, when viewed with contact lenses where the two contact lenses are different (usually chromatically opposite) colors, such as red and cyan. The picture contains two differently filtered colored images, one for each eye. When viewed through color coded contact lenses, an integrated stereoscopic image is revealed. FIGS. 17A and 17B are illustrations depicting contact lenses 1700 having colored areas configured for filtering left and right images of a 3-D display in accordance with one embodiment. In FIG. 17A, contact lens 1710 includes area 1730 configured with or tinted a first color. The first color is selected to filter for a second, preferably chromatically opposite, color. In FIG. 17B, contact lens 1720 includes area 1740 configured with or tinted using the second color. The second color is selected to filter for the first color.

In various embodiments, contact lenses 1700 have the first and second color embedded therein. In further embodiments, contact lenses 1700 may have the first and second color affixed to one or more outer surfaces of contact lens 1710 and 1720. Some examples of possible color schemes includes red-green, red-blue, red-cyan, variants of red-cyan (e.g., anachrome, mirachrome, Trioscopic, magenta-green (e.g., INFICOLOR), amber-dark blue (e.g., Color Code 3D), magenta-cyan, and narrow-band interference filters (e.g., Infitec). In addition, contact lenses for viewing 3D information can optionally be designed such that they can be worn on top of a regular contact lens which a user might be using for improving his/her vision.

In some embodiments, contact lenses may be used to view stereoscopic images. In general, stereoscopy (also called stereoscopic or 3-D imaging) refers to a technique for creating or enhancing the illusion of depth in an image by presenting two offset images separately to the left and right eye of the viewer. Two strategies may be used to accomplish this: have a viewer wear contact lenses to combine separate images from two offset sources or have the viewer wear contact lenses to filter offset images from a single source separated to each eye.

Figure 18A:
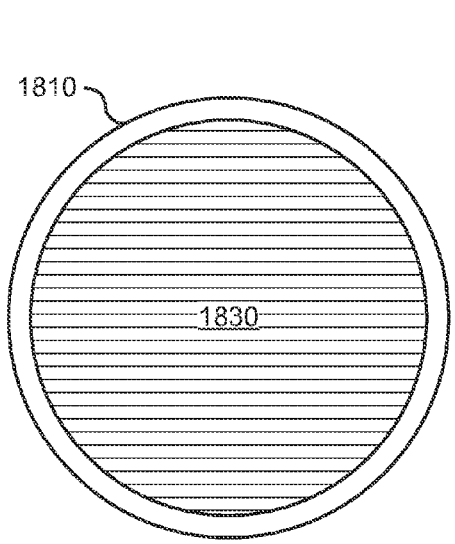
FIGS. 18A and 18B are illustrations depicting contact lenses having horizontally and vertically polarized areas configured for filtering left and right images of a 3-D display in accordance with one embodiment.
Figure 18B:
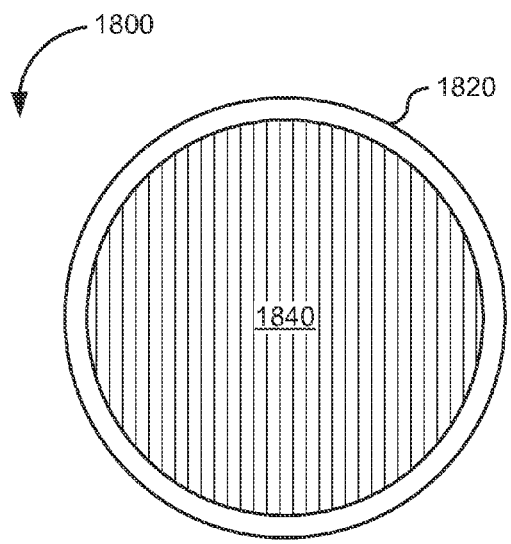

FIGS. 18A and 18B are illustrations depicting contact lenses 1800 having horizontally and vertically polarized areas configured for filtering left and right images of a 3-D display in accordance with one embodiment. In this example, contact lenses 1800 are linearly polarized. In FIG. 18A, contact lens 1810 includes area 1830 configured with a first linearly polarizing filter. The first linearly polarizing filter is selected to be transparent to light at a first linear polarization and to filter light at a second linear polarization. In FIG. 18B, contact lens 1820 includes area 1840 configured with a second linearly polarizing filter. The second linearly polarizing filter is selected be transparent to light at the second linear polarization and to filter light at the first linear polarization.

Thus, two images can be displayed superimposed onto the same screen through polarizing filters (e.g., orthogonal filters at 45 and 135 degrees). A viewer wears linearly polarized contact lenses 1800 each of which contain orthogonal polarizing filters oriented the same as the display. As each filter only passes light which is similarly polarized and blocks the orthogonally polarized light, each eye only sees one of the projected images, and the 3D effect is achieved.

Figures 19A, 19B:
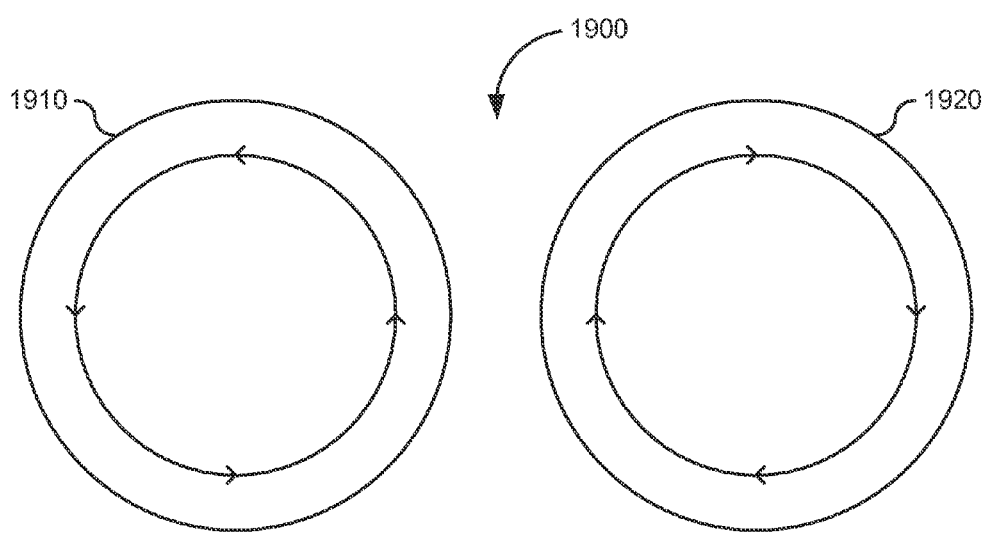
FIGS. 19A and 19B are illustrations depicting contact lenses having circularly polarized areas configured for filtering left and right images of a 3-D display in accordance with one embodiment.

FIGS. 19A and 19B are illustrations depicting contact lenses having circularly polarized areas configured for filtering left and right images of a 3-D display in accordance with one embodiment. In this example, contact lenses 1900 are circularly polarized. In FIG. 19A, contact lens 1910 is configured with a first circularly polarizing filter. The first circularly polarizing filter is selected to be transparent to light at a first circular polarization and to filter light at a second circular polarization. In FIG. 19B, contact lens 1920 is configured with a second circularly polarizing filter. The second circularly polarizing filter is selected be transparent to light at the second circular polarization and to filter light at the first circular polarization.

Thus, two images can be displayed superimposed onto the same screen through circular polarizing filters of opposite handedness. A viewer wears contact lenses 1900 each of which contain analyzing filters (circular polarizers mounted in reverse) of opposite handedness. Light that is left-circularly polarized is blocked by the right-handed analyzer, while right-circularly polarized light is extinguished by the left-handed analyzer.

Figure 20:
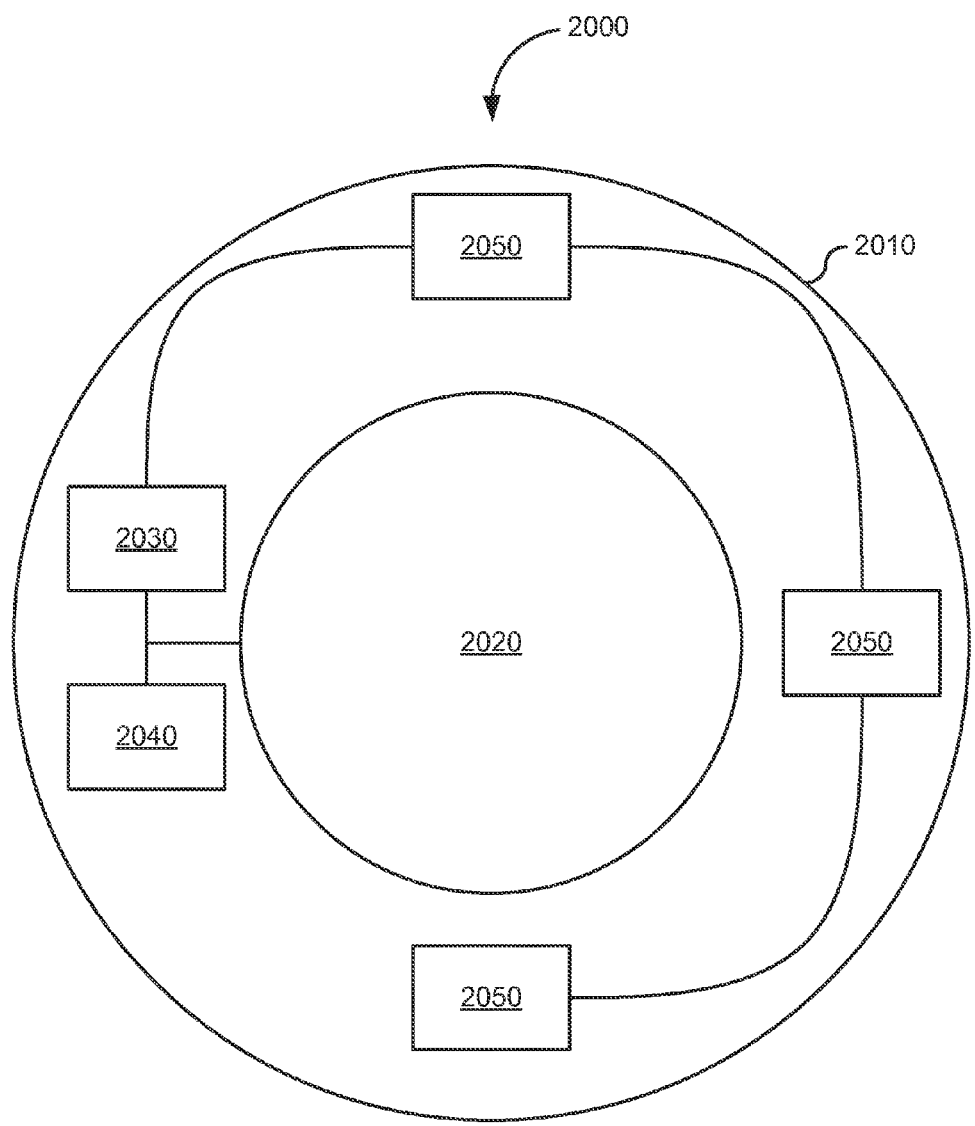
FIG. 20 is an illustration depicting a contact lens having circuitry configured for filtering left and right images of a 3-D display in accordance with one embodiment.

In further embodiments, contact lenses may include active elements that block or pass light through in synchronization with images on a 3D display (e.g., using the concept of alternate-frame sequencing). FIG. 20 is an illustration depicting contact lens 2000 having circuitry configured for filtering left and right images of a 3-D display in accordance with one embodiment. In this example, contact lens 2000 includes medium 2010, active material 2020, control circuitry 2030, power source 2040, and one or more antenna elements 2050.

Medium 2010 can include typical contact lens materials and is configured to support active material 2020, control circuitry 2030, power source 2040, and one or more antenna elements 2050. Active material 2020 is configured to alternate between a transparent state and an opaque state. Active material 2020 may have the property of becoming opaque (or dark) when voltage is applied, being otherwise transparent. One example of active material 2020 may include a liquid crystal layer.

Control circuitry 2030 includes one or more elements configured for controlling the state of active material 2020. Control circuitry may include a liquid crystal layer controller, memories, transceivers, and the like. In certain embodiments, control circuitry 2030 is powered by power source 2040. Power source 2040 may be optional in that control circuitry 2030 may draw power from antenna elements 2050 when energized by radio waves.

In further embodiments, contact lens 2000 is controlled by an infrared, radio frequency, DLP-Link or Bluetooth transmitter that sends a timing signal that allows control circuitry 2030 to control active material 2020 to alternately darken in synchronization with the refresh rate of a 3D display. Accordingly, the 3D display alternately displays different perspectives for each eye, using a technique called alternate-frame sequencing, which achieves the desired effect of each eye seeing only the image intended for it. In some aspects, contact lens 2000 remains in a transparent state such that when not powered up, a user can use contact lens 2000 for normal viewing.

Hardware Summary

Figure 21:
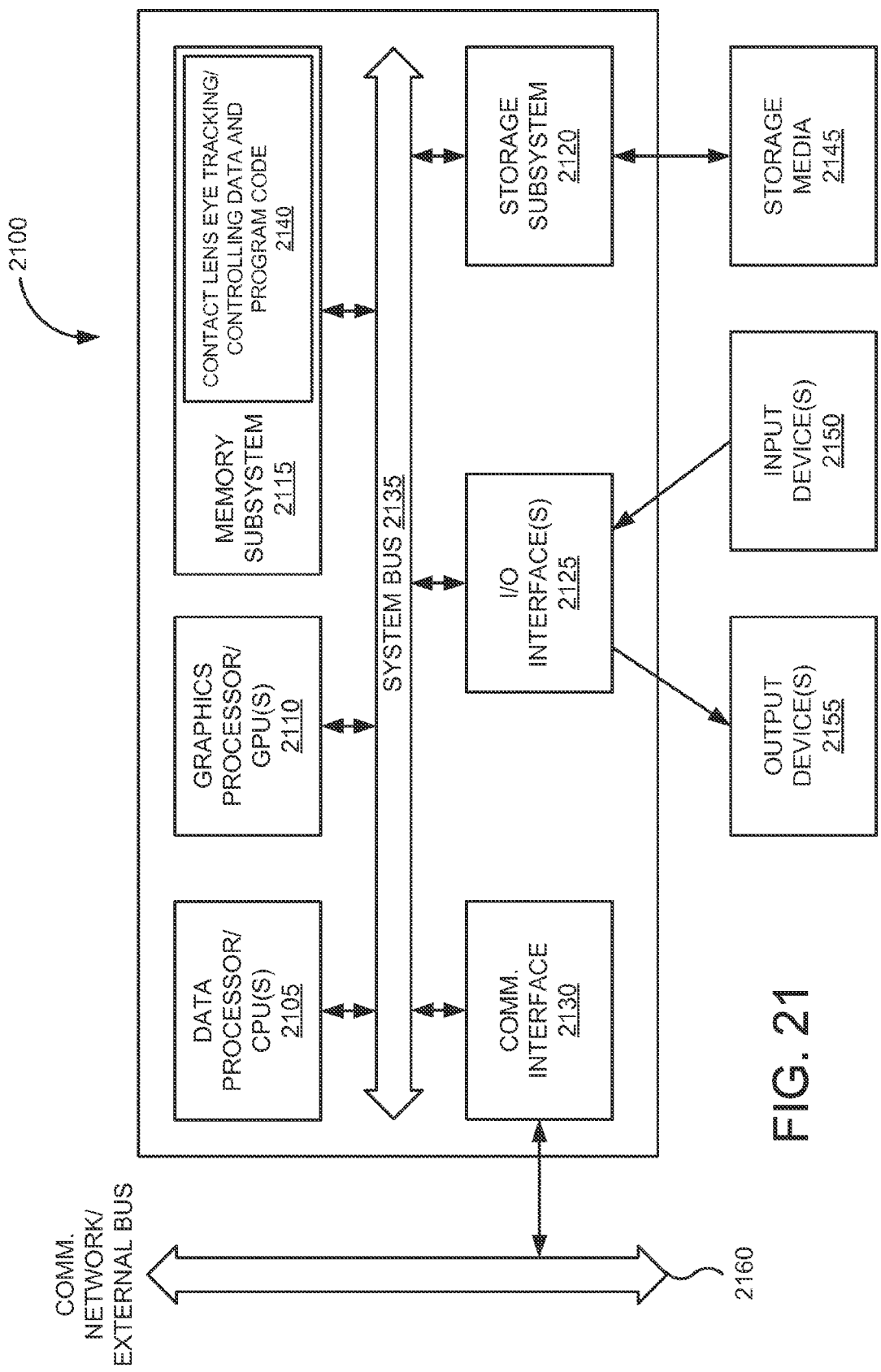
FIG. 21 is a block diagram of a computer system or information processing device that may incorporate an embodiment, be incorporated into an embodiment, or be used to practice any of the innovations, embodiments, and/or examples found within this disclosure.

FIG. 21 is a block diagram of computer system 2100 that may incorporate an embodiment, be incorporated into an embodiment, or be used to practice any of the innovations, embodiments, and/or examples found within this disclosure. FIG. 21 is merely illustrative of a computing device, general-purpose computer system programmed according to one or more disclosed techniques, or specific information processing device for an embodiment incorporating an invention whose teachings may be presented herein and does not limit the scope of the invention as recited in the claims. One of ordinary skill in the art would recognize other variations, modifications, and alternatives.

Computer system 2100 can include hardware and/or software elements configured for performing logic operations and calculations, input/output operations, machine communications, or the like. Computer system 2100 may include familiar computer components, such as one or more one or more data processors or central processing units (CPUs) 2105, one or more graphics processors or graphical processing units (GPUs) 2110, memory subsystem 2115, storage subsystem 2120, one or more input/output (I/O) interfaces 2125, communications interface 2130, or the like. Computer system 2100 can include system bus 2135 interconnecting the above components and providing functionality, such connectivity and inter-device communication. Computer system 2100 may be embodied as a computing device, such as a personal computer (PC), a workstation, a mini-computer, a mainframe, a cluster or farm of computing devices, a laptop, a notebook, a netbook, a tablet PC, a PDA, a smartphone, a consumer electronic device, a television, a gaming console, a portable gaming device, a portable media playback device, or the like.

The one or more data processors or central processing units (CPUs) 2105 can include hardware and/or software elements configured for executing logic or program code or for providing application-specific functionality. Some examples of CPU(s) 2105 can include one or more microprocessors (e.g., single core and multi-core) or micro-controllers. CPUs 2105 may include 4-bit, 8-bit, 12-bit, 16-bit, 32-bit, 64-bit, or the like architectures with similar or divergent internal and external instruction and data designs. CPUs 2105 may further include a single core or multiple cores. Commercially available processors may include those provided by Intel of Santa Clara, Calif. (e.g., x86, x86_64, PENTIUM, CELERON, CORE, CORE 2, CORE ix, ITANIUM, XEON, etc.), by Advanced Micro Devices of Sunnyvale, Calif. (e.g., X86, AMD_64, ATHLON, DURON, TURION, ATHLON XP/64, OPTERON, PHENOM, etc). Commercially available processors may further include those conforming to the Advanced RISC Machine (ARM) architecture (e.g., ARMv7-9), POWER and POWERPC architecture, CELL architecture, and or the like. CPU(s) 2105 may also include one or more field-gate programmable arrays (FPGAs), application-specific integrated circuits (ASICs), or other microcontrollers. The one or more data processors or central processing units (CPUs) 2105 may include any number of registers, logic units, arithmetic units, caches, memory interfaces, or the like. The one or more data processors or central processing units (CPUs) 2105 may further be integrated, irremovably or moveably, into one or more motherboards or daughter boards.

The one or more graphics processor or graphical processing units (GPUs) 2110 can include hardware and/or software elements configured for executing logic or program code associated with graphics or for providing graphics-specific functionality. GPUs 2110 may include any conventional graphics processing unit, such as those provided by conventional video cards. Some examples of GPUs are commercially available from NVIDIA, ATI, and other vendors. In various embodiments, GPUs 2110 may include one or more vector or parallel processing units. These GPUs may be user programmable, and include hardware elements for encoding/decoding specific types of data (e.g., video data) or for accelerating 2D or 3D drawing operations, texturing operations, shading operations, or the like. The one or more graphics processors or graphical processing units (GPUs) 2110 may include any number of registers, logic units, arithmetic units, caches, memory interfaces, or the like. The one or more data processors or central processing units (CPUs) 2105 may further be integrated, irremovably or moveably, into one or more motherboards or daughter boards that include dedicated video memories, frame buffers, or the like.

Memory subsystem 2115 can include hardware and/or software elements configured for storing information. Memory subsystem 2115 may store information using machine-readable articles, information storage devices, or computer-readable storage media. Some examples of these articles used by memory subsystem 2170 can include random access memories (RAM), read-only-memories (ROMS), volatile memories, non-volatile memories, and other semiconductor memories. In various embodiments, memory subsystem 2115 can include contact lens eye tracking/controlling data and program code 2140.

Storage subsystem 2120 can include hardware and/or software elements configured for storing information. Storage subsystem 2120 may store information using machine-readable articles, information storage devices, or computer-readable storage media. Storage subsystem 2120 may store information using storage media 2145. Some examples of storage media 2145 used by storage subsystem 2120 can include floppy disks, hard disks, optical storage media such as CD-ROMS, DVDs and bar codes, removable storage devices, networked storage devices, or the like. In some embodiments, all or part of contact lens eye tracking/controlling data and program code 2140 may be stored using storage subsystem 2120.

In various embodiments, computer system 2100 may include one or more hypervisors or operating systems, such as WINDOWS, WINDOWS NT, WINDOWS XP, VISTA, WINDOWS 7 or the like from Microsoft of Redmond, Wash., Mac OS or Mac OS X from Apple Inc. of Cupertino, Calif., SOLARIS from Sun Microsystems, LINUX, UNIX, and other UNIX-based or UNIX-like operating systems. Computer system 2100 may also include one or more applications configured to execute, perform, or otherwise implement techniques disclosed herein. These applications may be embodied as contact lens eye tracking/controlling data and program code 2140. Additionally, computer programs, executable computer code, human-readable source code, shader code, rendering engines, or the like, and data, such as image files, models including geometrical descriptions of objects, ordered geometric descriptions of objects, procedural descriptions of models, scene descriptor files, or the like, may be stored in memory subsystem 2115 and/or storage subsystem 2120.

The one or more input/output (I/O) interfaces 2125 can include hardware and/or software elements configured for performing I/O operations. One or more input devices 2150 and/or one or more output devices 2155 may be communicatively coupled to the one or more I/O interfaces 2125.

The one or more input devices 2150 can include hardware and/or software elements configured for receiving information from one or more sources for computer system 2100. Some examples of the one or more input devices 2150 may include a computer mouse, a trackball, a track pad, a joystick, a wireless remote, a drawing tablet, a voice command system, an eye tracking system, external storage systems, a monitor/display appropriately configured as a touch screen, a communications interface appropriately configured as a transceiver, or the like. In various embodiments, the one or more input devices 2150 may allow a user of computer system 2100 to interact with one or more non-graphical or graphical user interfaces to enter a comment, select objects, icons, text, user interface widgets, or other user interface elements that appear on a monitor/display device via a command, a click of a button, or the like.

The one or more output devices 2155 can include hardware and/or software elements configured for outputting information to one or more destinations for computer system 2100. Some examples of the one or more output devices 2155 can include a printer, a fax, a feedback device for a mouse or joystick, external storage systems, a monitor or other display device, a television, a communications interface appropriately configured as a transceiver, or the like. The one or more output devices 2155 may allow a user of computer system 2100 to view objects, icons, text, user interface widgets, or other user interface elements.

A display device or monitor may be used with computer system 2100 and can include hardware and/or software elements configured for displaying information. Some examples include familiar display devices, such as a television monitor, a cathode ray tube (CRT), a liquid crystal display (LCD), or the like.

Communications interface 2130 can include hardware and/or software elements configured for performing communications operations, including sending and receiving data. Some examples of communications interface 2130 may include a network communications interface, an external bus interface, an Ethernet card, a modem (telephone, satellite, cable, ISDN), (asynchronous) digital subscriber line (DSL) unit, FireWire interface, USB interface, or the like. For example, communications interface 2130 may be coupled to communications network/external bus 2180, such as a computer network, to a FireWire bus, a USB hub, or the like. In other embodiments, communications interface 2130 may be physically integrated as hardware on a motherboard or daughter board of computer system 2100, may be implemented as a software program, or the like, or may be implemented as a combination thereof.

In various embodiments, computer system 2100 may include software that enables communications over a network, such as a local area network or the Internet, using one or more communications protocols, such as the HTTP, TCP/IP, RTP/RTSP protocols, or the like. In some embodiments, other communications software and/or transfer protocols may also be used, for example IPX, UDP or the like, for communicating with hosts over the network or with a device directly connected to computer system 2100.

As suggested, FIG. 21 is merely representative of a general-purpose computer system appropriately configured for implementing or incorporating various embodiments of an invention presented within this disclosure or a specific data processing device capable of implementing or incorporating various embodiments of an invention presented within this disclosure. Many other hardware and/or software configurations may be apparent to the skilled artisan which are suitable for use in implementing an invention presented within this disclosure or with various embodiments of an invention presented within this disclosure. For example, a computer system, a gaming device, a television, or other data processing device may include desktop, home theater, portable, rack-mounted, or tablet configurations. Additionally, a computer system or information processing device may include a series of networked computers or clusters/grids of parallel processing devices. In still other embodiments, a computer system or information processing device may perform techniques described above as implemented upon a chip or an auxiliary processing board.

Various embodiments of any of one or more inventions whose teachings may be presented within this disclosure can be implemented in the form of logic in software, firmware, hardware, or a combination thereof. The logic may be stored in or on a machine-accessible memory, a machine-readable article, a tangible computer-readable medium, a computer-readable storage medium, or other computer/machine-readable media as a set of instructions adapted to direct a central processing unit (CPU or processor) of a logic machine to perform a set of steps that may be disclosed in various embodiments of an invention presented within this disclosure. The logic may form part of a software program or computer program product as code modules become operational with a processor of a computer system or an information-processing device when executed to perform a method or process in various embodiments of an invention presented within this disclosure. Based on this disclosure and the teachings provided herein, a person of ordinary skill in the art will appreciate other ways, variations, modifications, alternatives, and/or methods for implementing in software, firmware, hardware, or combinations thereof any of the disclosed operations or functionalities of various embodiments of one or more of the presented inventions.

The disclosed examples, implementations, and various embodiments of any one of those inventions whose teachings may be presented within this disclosure are merely illustrative to convey with reasonable clarity to those skilled in the art the teachings of this disclosure. As these implementations and embodiments may be described with reference to exemplary illustrations or specific figures, various modifications or adaptations of the methods and/or specific structures described can become apparent to those skilled in the art. All such modifications, adaptations, or variations that rely upon this disclosure and these teachings found herein, and through which the teachings have advanced the art, are to be considered within the scope of the one or more inventions whose teachings may be presented within this disclosure. Hence, the present descriptions and drawings should not be considered in a limiting sense, as it is understood that an invention presented within a disclosure is in no way limited to those embodiments specifically illustrated.

Accordingly, the above description and any accompanying drawings, illustrations, and figures are intended to be illustrative but not restrictive. The scope of any invention presented within this disclosure should, therefore, be determined not with simple reference to the above description and those embodiments shown in the figures, but instead should be determined with reference to the pending claims along with their full scope or equivalents.

What is claimed is:

1. A contact lens system for viewing 3D information, the contact lens system comprising:
    material forming a lens of suitable size to fit a wearer's eye and extend over at least a portion of the sclera of the wearer's eye, wherein a portion of the material is configured to filter the 3D information to obtain a portion of the 3D information designated for the wearer's eye;
    one or more reflective elements associated with the material forming the lens, the one or more reflective elements configured to reflect a predetermined portion of the electromagnetic spectrum;
    one or more video-based sensors configured to track the one or more reflective elements, the one or more video-based sensors configured to generate and transmit tracking information associated with the tracking of the one or more reflective elements; and
    a computing device configured to determine eye gaze information based on the tracking information, and configured to perform one or more actions using the eye gaze information, wherein the one or more actions are associated with the 3D information being viewed.

2. The contact lens system of claim 1, wherein the lens has an optical zone and a peripheral zone.

3. The contact lens system of claim 2, wherein the one or more reflective elements associated with the material forming the lens comprise a plurality of reflective elements clustered in a portion of the optical zone.

4. The wearable apparatus of claim 2, wherein the one or more reflective elements associated with the material forming the lens comprise a set of circular bands distributed in the peripheral zone.

5. The wearable apparatus of claim 2, wherein the one or more reflective elements associated with the material forming the lens comprise a set of reflective shapes distributed in the peripheral zone.

6. The contact lens system of claim 1, wherein the portion of the material configured to filter 3D information to obtain a portion of the 3D information designated for the wearer's eye comprises at least one of a color filter layer associated with at least one of a plurality chromatically opposite colors, a polarization filter layer associated with at least one of a plurality of light polarizations, or a liquid crystal layer that obscures the optical zone to block a portion of the 3D information that is not designated for the wearer's eye.

7. The contact lens system of claim 1, further comprising:
a second computing device configured to perform one or more actions based on the tracking information.

8. The contact lens system of claim 7, further comprising:
a wearable apparatus, wherein the second computing device is connected to the wearable apparatus.

9. The contact lens system of claim 1, further comprising:
a wearable apparatus, wherein the lens and one or more video-based sensors are coupled to the wearable apparatus.

10. The eye tracking system of claim 9, wherein the wearable apparatus is a pair of glasses.

11. The eye tracking system of claim 9, wherein the wearable apparatus is configured to be worn around the neck of the wearer.

12. The eye tracking system of claim 1, further comprising:
material forming a second lens of suitable size to fit a wearer's eye and including one or more magnetic elements associated with the material forming the second lens;
one or more magnetic sensors configured to track the second lens, the one or more magnetic sensors configured to generate second tracking information associated with the tracking of the second lens; and
a computing device configured to perform one or more actions based on the tracking information and the second tracking information.

13. The wearable apparatus of claim 1, wherein the one or more reflective elements associated with the material forming the lens reflect infrared or near infrared light.

* * * * *